US009763465B2

(12) United States Patent
Sprenger

(10) Patent No.: US 9,763,465 B2
(45) Date of Patent: Sep. 19, 2017

(54) OLIGOSACCHARIDE COMPOSITION FOR TREATING ACUTE RESPIRATORY TRACT INFECTIONS

(75) Inventor: Norbert Sprenger, Savigny (CH)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 13/988,975

(22) PCT Filed: Nov. 21, 2011

(86) PCT No.: PCT/EP2011/070563
§ 371 (c)(1),
(2), (4) Date: May 22, 2013

(87) PCT Pub. No.: WO2012/076323
PCT Pub. Date: Jun. 14, 2012

(65) Prior Publication Data
US 2013/0236424 A1 Sep. 12, 2013

(30) Foreign Application Priority Data
Nov. 23, 2010 (EP) .................................. 10192230

(51) Int. Cl.
A01N 63/00 (2006.01)
A61K 39/395 (2006.01)
A23L 1/29 (2006.01)
A61K 31/702 (2006.01)
A61K 35/745 (2015.01)
A61K 35/747 (2015.01)
A61K 45/06 (2006.01)
A61K 31/726 (2006.01)
A61K 35/741 (2015.01)
A23L 33/00 (2016.01)
A23L 33/10 (2016.01)
A23L 33/18 (2016.01)
A23L 33/21 (2016.01)

(52) U.S. Cl.
CPC .............. A23L 1/296 (2013.01); A23L 33/10 (2016.08); A23L 33/18 (2016.08); A23L 33/21 (2016.08); A23L 33/40 (2016.08); A61K 31/702 (2013.01); A61K 31/726 (2013.01); A61K 35/741 (2013.01); A61K 35/745 (2013.01); A61K 35/747 (2013.01); A61K 45/06 (2013.01); A23V 2002/00 (2013.01)

(58) Field of Classification Search
CPC ............................. A01N 63/00; A61K 39/365
See application file for complete search history.

(56) References Cited

U.S. PATENT DOCUMENTS 6,045,854 A * 4/2000 Prieto ...................... A23L 33/40
426/658
6,863,918 B2 * 3/2005 Bindels et al. ............... 426/590
7,893,041 B2 * 2/2011 Morrow ................ A61K 31/702
514/3.1
2003/0060445 A1 * 3/2003 Wilson .................. A61K 31/715
514/54
2010/0233198 A1 * 9/2010 Fichot ................ A61K 31/7028
424/184.1

FOREIGN PATENT DOCUMENTS

| EP | WO 2005/049813 A1 * | 6/2005 | ............... C12N 7/00 |
|---|---|---|---|
| EP | 1629850 | 3/2006 | |
| EP | 2044851 | 4/2009 | |
| EP | 2060257 | 5/2009 | |
| WO | 2005055944 | 6/2005 | |
| WO | 2007144334 | 12/2007 | |
| WO | 2009077352 | 6/2009 | |
| WO | 2011008087 | 1/2011 | |
| WO | 2012069416 | 5/2012 | |
| WO | 2012076321 | 6/2012 | |
| WO | 2012076322 | 6/2012 | |

OTHER PUBLICATIONS

Fraser et al. (Enterobacter Infections Clinical Presentations. Medscape. Updated 2013. pp. 1-8).*
Olivares et al. (Antimicrobial potential of four Lactobacillus strains isolated from breast milk. Journal of Applied Microbiology. (2006) 101:72-79).*
Duncan et al. (Exclusive Breast-Feeding for at Least 4 Months Protects Against Otitis Media. Pediatrics (1993) 91(5):867-873).*
BabyCenterCommunity Post. 2010.*
Asakuma et al. (Sialyl Oligosaccharides of Human Colostrum: Changes in Concentration during the First Three Days of Lactation. Biosci. Biotechnol. Biochem. 71 (6), 1447-1451, 2007).*
Chonmaitree et al. (Viral Upper Respiratory tract Infection and Otitis Media Complication in Young Children. Clinical Infections Diseases; 46:815-23, 2008).*
Hall et al. (Bronchiolitis. Nov. 2010).*
Tan et al. (Determination of Human Milk Oligosaccharides in Human Breast Milk by HPAE-PAD with On-Line Sample Cleanup. Thermoscientific, pp. 1-6. 2015).*
Debarbieux et al. "Bacteriophages Can Treat and Prevent Psudomonas aeruginosa Lung Infections" The Journal of Infectious Diseases, 2010, vol. 201, pp. 1096-1104.
Fornarini et al. "Human Milk 90K (Mac-2 BP): Possible Protective Effects Against Acute Respiratory Infections" Clinical and Experimental Immunology, 1999, vol. 115, pp. 91-94.

(Continued)

Primary Examiner — Scott Long
Assistant Examiner — Natalie Moss
(74) Attorney, Agent, or Firm — K&L Gates LLP

(57) ABSTRACT

The inventions discloses a composition comprising at least one N-acetyl lactosamine, at least one sialylated oligosaccharide and at least one fucosylated oligosaccharide, for use in preventing acute respiratory infections (ARI) and/or relieving symptoms of said ARI infections. Preferably said composition is a starter infant formula. Said acute respiratory infection is in particular bronchiolitis or otitis.

22 Claims, 3 Drawing Sheets

(56) References Cited

OTHER PUBLICATIONS

Sheard, "Breast-Feeding Protects Against Otitis Media" Nutrition Reviews, 1993, vol. 51, No. 9, pp. 275-277. XP008134479.
Bertino et al. "Effects of Holder Pasteurization on Human Milk Oligosaccharides" International Journal of Immunopathology and Pharmacology, 2008, vol. 21, No. 2, pp. 381-385. XP008134308.
Beijers et al. "Composition of Premature Breast-Milk During Lactation: Constant Digestible Protein Content (As in Full Term Milk)" Early Human Development, 1992, vol. 29, pp. 351-356.
Flanders Stepans et al. "Early Consumption of Human Milk Oligosaccharides Is Inversely Related to Subsequent Rick of Respiratory and Enteric Disease in Infants" Breastfeeding Medicine, vol. 1, No. 4, 2006, pp. 207-215, XP009157661.
Ruhaak et al. "Advances in Analysis of Human Milk Oligosaccharides1-3" Advances in Nutrition, 2012, vol. 3, No. 3, pp. 406S-414S.
European Office Action for Application No. 11 784 695.6-1453, dated Jun. 29, 2015, 8 pages.

\* cited by examiner

Figure 1

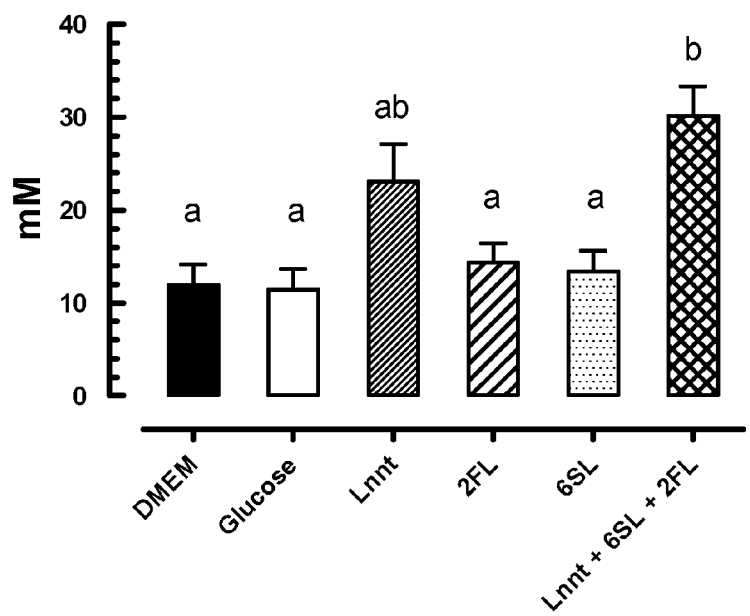

*Figure 1.* Experimental results showing metabolic stimulation of a bifidobacterium (B. longum subsp infantis) in DMEM culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL. (n=6; mean with SEM are shown; significance by ANOVA indicated).
Note: Only the blend of LNnT, 6SL and 2FL stimulated significantly the production of acetate.

Figure 2

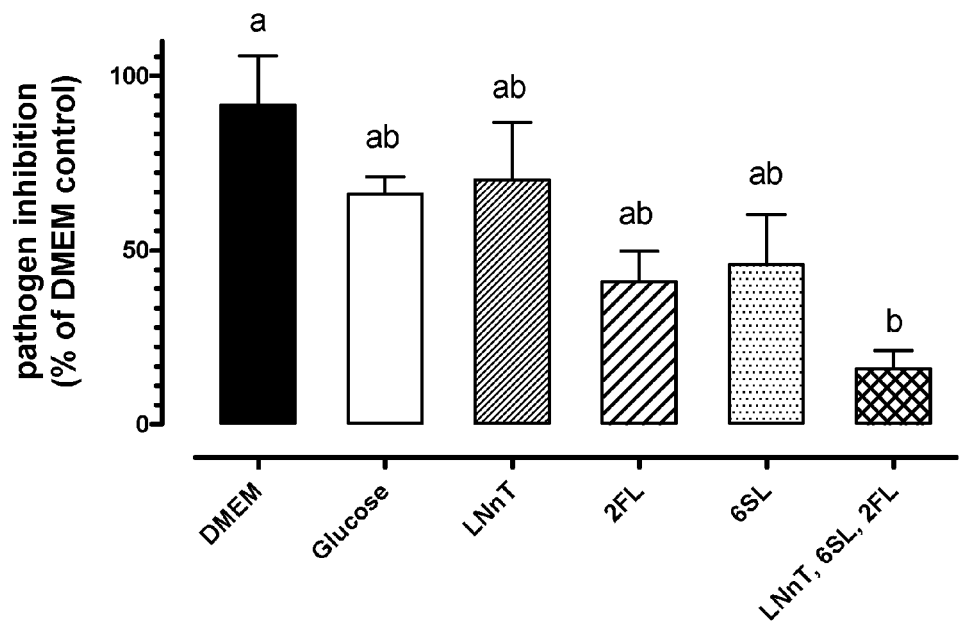

*Figure 2. Experimental results showing in vitro growth of a bifidobacterium (B. longum subsp infantis) in culture medium either without additional carbohydrates or with additional glucose (Glc), or lacto-N-neoteraose (LNnT) or 2'fucosyllactose (2FL) or 2'fucosyllactose (2FL) or 6'sialyllactose (6SL) or a blend of LNnT, 6SL and 2FL.. (n=4; mean with SEM are shown; significance by ANOVA (p<0.01) indicated by small letters).*

*Figure 3.* Experimental results showing number of respiratory infections in infants up to 2 years of age that were either fed a milk that contained low amounts (<2g/l) or high amounts (≥2g/l) of an oligosaccharide blend composed of 2FL, LNnT and 6SL. (statistical significance is indicated).

OLIGOSACCHARIDE COMPOSITION FOR TREATING ACUTE RESPIRATORY TRACT INFECTIONS

CROSS REFERENCE TO RELATED APPLICATIONS

The present application is a National Stage of International Application No. PCT/EP2011/070563, filed on Nov. 21, 2011, which claims priority to European Patent Application No. 10192230.0, filed Nov. 23, 2010, the entire contents of which are being incorporated herein by reference.

FIELD OF THE INVENTION

This invention relates to a composition for use in preventing acute respiratory (tract) infections (ARI) and/or relieving symptoms of said ARI.

BACKGROUND OF THE INVENTION

Infections of the respiratory tract are very common, especially in infants and small children. For example, in the first year of life, an infant will often experience from three to six such infections. Such infections are usually of bacterial origin and often follow a viral infection such as influenza. Examples of bacterial infections of the respiratory tract include pneumonia, bronchiolitis, sinusitis, pharyngitis, and otitis media.

Acute respiratory infections (ARI) are secondary bacterial infections (as opposed to upper respiratory tract infections). They may lead to middle ear infection, bronchitis, bronchiolitis, pneumonia, sinusitis, pharyngitis, otitis or strep throat. People with chronic lung disease, asthma, diabetes, or a weakened immune system are more likely to develop these complications.

Frequent acute respiratory infections (ARI) are often associated with acute otitis media. This is an infection of the middle ear in which the Eustachian tube connecting the cavity of the middle ear with the external environment via the mouth becomes inflamed and then blocked, trapping bacteria inside the middle ear. In severe cases, the tympanic membrane may burst under pressure allowing the infected liquid to reach the inner ear. This is a potentially dangerous situation which can lead to permanently impaired hearing if left untreated.

Acute otitis media appears to be linked to the activity of pathogenic bacteria commonly found in the indigenous microbiota of the naso-pharyngeal cavity. Quantitatively, the most significant pathogens are *Streptococcus pneumoniae* (35% of case), untypeable *Haemophilus influenzae* (30% of cases) and *Moraxella catarrhalis* (10% of cases).

50% of children will have had a least one episode of acute otitis media in the first year of their life and 35% of children between one and three years of age have recurrent episodes of acute otitis media.

Bronchiolitis is another common illness of the respiratory tract caused by an infection affecting the tiny airways, called the bronchioles that lead to the lungs. As these airways become inflamed, they swell and fill with mucus, making breathing difficult.

Although it is often a mild illness, some infants are at risk of contracting a more severe disease requiring hospitalization. The conditions which increase the risk of severe bronchiolitis include prematurity, prior chronic heart or lung disease, and a weakened immune system due to illness or medications.

Young children who have had bronchiolitis may be more likely to develop asthma later in life, but it is unclear whether the illness causes or triggers asthma, or whether children who eventually develop asthma were simply more prone to developing bronchiolitis as infants.

Bronchiolitis is usually caused by a viral infection, which is in general due to the respiratory syncytial virus (RSV). RSV infections are responsible for more than half of all cases of bronchiolitis and are most widespread in the winter and early spring. Other viruses associated with bronchiolitis include rhinovirus, influenza (flu), and human metapneumovirus.

From the foregoing, it may be seen that there is a need for an effective method for preventing the ARI infections and/or relieving the symptoms of ARI, bronchiolitis and acute otitis media (or otitis) in particular.

Human milk oligosaccharides (HMOs) are, collectively, the third largest solid constituents in human milk, after lactose and fat. HMO usually consists of lactose at the reducing end with a carbohydrate core that often contains a fucose or a sialic acid at the non-reducing end. There are approximately one hundred milk oligosaccharides that have been isolated and characterized, however these represent only a very small portion of the total number remaining to be characterized.

In the past, infant formulae were developed using HMO ingredients, such as fucosylated oligosaccharides, lacto-N-tetraose, lacto-N-neotetraose, or sialylated oligosaccharides, for different purposes.

EP 0 975 235 B1 from Abbott Laboratories describes a synthetic nutritional composition comprising one or more human milk oligosaccharides, wherein the HMOs in the composition are chosen among a group of eight HMOs (3-fucosyllactose, lacto-N-fucopentaose III, lacto-N-fucopentaose II, difucosyllactose, 2'-fucosyllactose, lacto-N-fucopentaose I, lacto-N-neotetraose and lacto-N-fucopentaose V) wherein said composition is intended for cases of normal, healthy infants, children, adults or subjects having specialized needs such as those that accompany certain pathological conditions. This European patent states that, generally speaking, oligosaccharides protect infants from viral and bacterial infections of the respiratory, gastrointestinal and uro-genital tracts.

From the foregoing, it may be seen that there is a need for an effective nutritional composition for preventing acute respiratory infections and/or relieving symptoms of acute respiratory infections, particularly in infants and young children, and which may be conveniently and safely administered.

There is a need to alleviate the symptoms and/or to reduce the severity, frequency, occurrence and/or duration of ARI, in particular otitis or bronchiolitis, in susceptible individuals, especially infants, and more specifically infants presenting a history of such conditions or risk factors.

There is a need for such intervention that reserves the metabolic balance of such fragile individuals and thus is not accompanied by side effects such as the disturbance of the immune system or the change in the inflammation status.

There is a need to improve of the symptoms and to alleviate the conditions often associated of acute respiratory infections, in particular otitis and bronchiolitis, by a non-drug-based intervention that is compatible with fragile individuals like infants or babies.

These conditions can include the effects on sleep quality and/or quantity, pain, hyper or hypo-activity, and/or crying time.

SUMMARY OF THE INVENTION

The present inventors have found surprisingly that a composition comprising a mixture of specific human oligosaccharides is particularly effective for use in preventing acute respiratory infections (ARI) and/or relieving symptoms of acute respiratory infections, and in particular preventing and/or relieving symptoms of bronchiolitis or otitis.

Accordingly, the present invention provides a composition comprising at least one N-acetyl lactosamine, at least one sialylated oligosaccharide and at least one fucosylated oligosaccharide, for use in preventing Acute Respiratory Infections and/or relieving symptoms of Acute Respiratory Infections.

BRIEF DESCRIPTION OF THE DRAWINGS

FIG. 1 illustrates the experimental results showing metabolic stimulation of a bifidobacterium without additional carbohydrates or with additional glucose (Glc), or lacto-N-neoteraose (LNnT) or 2' fucosyllactose (2FL) or 6' sialyllactose (6SL) or a blend of LNnT, 6SL and 2FL.

FIG. 2 illustrates the experimental results showing in vitro growth of a bifidobacterium without additional carbohydrates or with additional glucose (Glc), or lacto-N-neoteraose (LNnT) or 2 fucosyllactose (2FL) or 2 fucosyllactose (2FL) or 6' sialyllactose (6SL) or a blend of LNnT, 6SL and 2FL.

DETAILED DESCRIPTION OF THE INVENTION

Figure 3:
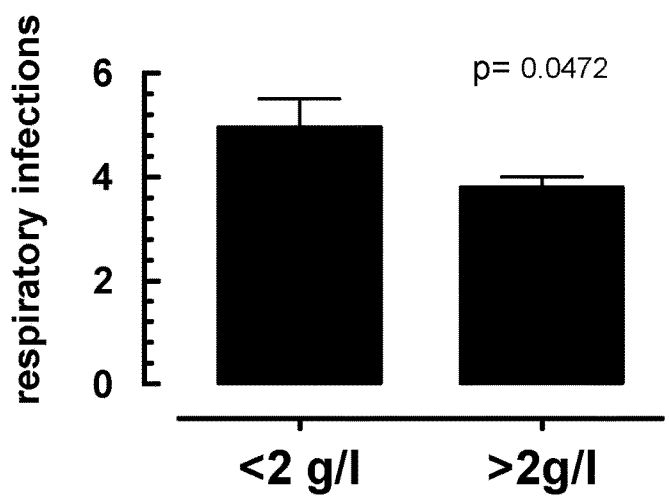
FIG. 3 illustrates the experimental results showing number of respiratory infections in infants fed a milk that contained low amounts or high amounts of an oligosaccharide blend composed of 2FL, LNnT and 6SL.

As used herein, the following terms have the following meanings.

The term "infant" means a child under the age of 12 months.

The term "young child" means a child aged between one and three years.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four months of life.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "weaning period" means the period during which the mother's milk is substituted by other food in the diet of an infant.

The term "preventing the ARI" means the prevention and the reduction of frequency and/or occurrence and/or severity and/or duration of ARI, in particular otitis and bronchiolitis. Occurrence is related to the number of any ARI. Frequency is related to the number of the same ARI. This prevention encompasses the reduction of frequency and/or of severity of said ARI later in life. The term "later in life" encompasses the effect after the termination of the intervention. The effect "later in life" can be preferably 2 to 4 weeks, 2 to 12 months or years (e.g. 2, 5, 10 years) after the termination of said intervention.

The term "relieving symptoms of ARI" means reducing the symptoms of ARI, especially those of bronchiolitis or otitis, and in particular easing the breathing process and/or diminishing the pain and/or easing the sleep and/or stabilizing the activity of infants and young children suffering from ARI.

The term "nutritional composition" means a composition which nourishes a subject. This nutritional composition is usually to be taken orally or intraveinously, and it usually includes a lipid or fat source and a protein source.

The term "synthetic mixture" means a mixture obtained by chemical and/or biological means, which can be chemically identical to the mixture naturally occurring in mammalian milks.

The term "hypoallergenic nutritional composition" means a nutritional composition which is unlikely to cause allergic reactions.

The term "sialylated oligosaccharide" means an oligosaccharide having a sialic acid residue.

The term "fucosylated oligosaccharide" means an oligosaccharide having a fucose residue.

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J. Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" *Trends Food Sci. Technol.* 1999:10 107-10).

An "allergy" is an allergy which has been detected by a medical doctor and which can be treated occasionally or in a more durable manner.

All percentages are by weight unless otherwise stated.

The composition according to the invention is preferably a hypoallergenic composition.

Said composition contains at least one N-acetyl-lactosamine. That is to say that it contains N-acetyl-lactosamine and/or an oligosaccharide containing N-acetyl-lactosamine. Suitable oligosaccharides containing N-acetyl-lactosamine include lacto-N-tetraose (LNT) and lacto-N-neotetraose (LNnT).

Thus, according to the invention, the N-acetyl-lactosamine is preferably selected from the group comprising lacto-N-tetraose (LNT) and lacto-N-neotetraose (LNnT).

LNT and LNnT may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetyl-hexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

Preferably the composition according to the invention contains from 0.1 to 3 g N-acetyl-lactosamine lactose(s)/100 g composition on a dry weight basis.

According to the invention, the sialylated oligosaccharide is selected from the group comprising 3'-sialyllactose and 6'-sialyllactose. Preferably, both 3'-sialyllactose and 6'-sialyllactose are present in said composition. In this embodiment, the ratio between 3'-sialyllactose and 6'-sialyllactose lies preferably in the range between 5:1 and 1:2.

The 3'- and 6'-forms of sialyllactose may be isolated by chromatographic or filtration technology from a natural source such as animal milks. Alternatively, they may be produced by biotechnological means using specific sialyl-transferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

Preferably the composition according to the invention contains from 0.05 to 2 g, more preferably 0.1 to 2 g, of sialylated oligosaccharide(s) per 100 g of composition on a dry weight basis.

The fucosylated oligosaccharide may be selected from the group comprising 2'-fucosyllactose, 3-fucosyllactose, difucosyllactose, lacto-N-fucopentaoses (that is to say lacto-N-fucopentaose I, lacto-N-fucopentaose II, lacto-N-fucopentaose III and lacto-N-fucopentaose V), lacto-N-difucohexaose I, fucosyllacto-N-hexaose, Difucosyllacto-N-hexaose I and Difucosyllacto-N-neohexaose II. A particularly preferred fucosylated oligosaccharide is 2'-fucosyllactose (2-FL).

The fucosylated oligosaccharide may be isolated by chromatography or filtration technology from a natural source such as animal milks. Alternatively, it may be produced by biotechnological means using specific fucosyltransferases and/or fucosydase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

Preferably, the composition according to the invention contains from 0.1 to 3 g of fucosylated oligosaccharide(s) per 100 g of composition on a dry weight basis.

In a preferred embodiment, the composition of the invention comprises from 0.05 to 3 g of the total amount of N-acetylated lactosamine(s), sialylated oligosaccharide(s) and fucosylated oligosaccharide(s) per 100 g of composition.

The composition of the invention can further comprise at least one probiotic bacterial strain, said probiotic bacterial strain preferably being Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus reuteri* sold by BioGaia A. B under the trademark Reuteri, *Lactobacillus johnsonii* CNCM I-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

Preferably, the composition according to the invention contains from 10e3 to 10e12 cfu of probiotic bacterial strain, more preferably between 10e7 and 10e12 cfu, per g of composition on a dry weight basis.

The composition of the invention can further comprise at least one prebiotic, usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such a fructooligosaccharides (FOS) and galactooligosaccharides (GOS). A combination of prebiotics may be used such as 90% GOS with 10% short chain fructo-oligosaccharides such as in the product by BENEO-Orafti sold under the trademark Orafti® oligofructose (previously Raftilose®) or 10% inulin such as in the product sold by BENEO-Orafti under the trademark Orafti® inulin (previously Raftiline®). A particularly preferred combination of prebiotics is 70% short chain fructo-oligosaccharides and 30% inulin, which is a product sold by BENEO-Orafti under the trademark "Prebio 1".

The composition of the invention can further comprise at least one phage (bacteriophage) or a mixture of phages, preferably directed against pathogenic *Streptococci Haemophilus, Moraxella* and *Staphylococcie.*

The composition according to the invention is preferably a synthetic nutritional composition. In this case, it can be a starter infant formula, an infant formula, a baby food, an infant cereal composition, a follow-on formula or a growing-up milk, and said composition is preferably a starter infant formula.

According to a preferred embodiment, the composition according to the invention is for use in infants and young children who suffer from ARI.

The composition according to the invention can be for use before and/or during a weaning period.

The composition of the invention can further comprise at least one phage or a mixture of phages for example directed against pathogenic *Streptococci Haemophilus, Moraxella, Staphylococci*.

Thus preferably the composition according to the invention is for use in the easing of the breathing process, the decrease of pain, the easing of sleep, and/or the relieving of symptoms in infants with ARI or having early symptoms of ARI.

An ARI is in particular bronchiolitis or otitis.

The invention includes also the use of a composition comprising at least one N-acetyl lactosamine, at least one sialylated oligosaccharide and at least one fucosylated oligosaccharide, as a synthetic nutritional agent, for the prevention and/or treatment of Acute Respiratory Infections, preferably bronchiolitis or otitis.

This use encompasses the case where the composition is a supplement, preferably provided in the form of unit doses.

All the uses stated above are particularly intended for infants and young children. The compositions and uses as per the present invention are particularly suited for infants and children at risk of respiratory tract infections and/or inflammation, having a family history of respiratory tract infections or inflammation, or having already experienced some episodes of respiratory tract infections or inflammation (and/or respiratory allergies). In one embodiment the composition and uses of the invention apply to teenagers or adults at risk of respiratory tract infections or inflammation or having experienced episodes of respiratory tract infections or inflammation (and/or respiratory allergies).

Without wishing to be bound by theory, the inventors believe that the efficacy of the combination of oligosaccharides described above in preventing ARI and/or relieving symptoms of ARI, may be a result of a synergistic interaction of events triggered by the combination of oligosaccharides described above. On the one hand commensal oropharyngeal microbiota are promoted and on the other hand potentially pathogenic microbes are demoted. For example it is well known that adherence of numerous oropharyngeal pathogens is slowed down by specific soluble milk oligosaccharides (see above). This combination of promotion and demotion is believed to lead to the establishment of the oropharyngeal microbiota with optimal and balanced (i) ecological niche occupation, (ii) microbiota-host interaction and (iii) ecological stability. Meaning that (i) a stable oropharyngeal ecological equilibrium is maintained even upon exogenous abiotic and biotic challenges. Hence, potentially infective agents are outcompeted beyond the intervention period and cannot easily establish and cause the ARI disease.

The oligosaccharides may be administered in the same composition or may be administered sequentially.

If the age group of 0 to 12 months of life is to be addressed, the composition is preferably a nutritional composition consumed in liquid form. It may be a nutritionally complete formula such as an infant formula, a follow-on formula or a growing-up milk.

Alternatively for the group of young children group, the composition may be a juice drink or other chilled or shelf stable beverage or a soup, for example, or a baby food, or an infant cereal composition.

The composition according to the invention also contains a protein source, preferably in an amount below 2.0 g per 100 kcal, even more preferably in an amount below 1.8 g per 100 kcal. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cow's milk allergy. In general, hydrolyzed proteins may reduce the risk of allergies (to cow milk or to other allergens). If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source. The composition according to the present invention generally contains a carbohydrate source. This is particularly preferable in the case where the nutritional composition of the invention is an infant formula. In this case, any carbohydrate source conventionally found in infant formulae such as lactose, saccharose, maltodextrin, starch and mixtures thereof may be used although the preferred source of carbohydrates is lactose. The composition according to the present invention generally contains a source of lipids. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. The fat source preferably has a ratio of n-6 to n-3 fatty acids of about 5:1 to about 15:1; for example about 8:1 to about 10:1.

The nutritional composition of the invention also contains preferably all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, and the like.

A composition according to the invention will now be described by way of example.

The formula may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The N-acetyl-lactosamine(s), sialylated oligosaccharide(s) and fucosylated oligosaccharide(s) will be added at this stage if the final product is to have a liquid form. If the final product is to be a powder, the oligosaccharides may likewise be added at this stage if desired. The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

The homogenised mixture is transferred to a suitable drying apparatus such as a spray dryer or freeze dryer and converted to powder. The powder should have a moisture content of less than about 5% by weight. The N-acetyl-lactosamine(s), sialylated oligosaccharide(s) and fucosylated oligosaccharide(s) may be added at this stage by dry-mixing, or by blending them in a syrup form of crystals, along with the probiotic bacterial strain(s) if used, and spray-dry (or freeze-dry).

If a liquid composition is preferred, the homogenised mixture may be sterilised then aseptically filled into suitable containers or may be first filled into the containers and then retorted.

In another embodiment, the composition of the invention may be a supplement including the N-acetyl-lactosamine(s), sialylated oligosaccharide(s) and fucosylated oligosaccharide(s) in an amount sufficient to achieve the desired effect in an individual. This form of administration is more suited to older children and adults. Preferably the daily dose of the N-acetyl-lactosamine(s) is from 0.1 to 3 g, the daily dose of the sialylated oligosaccharide(s) is from 0.1 to 2 g, and the daily dose of the fucosylated oligosaccharide(s) is from 0.1 to 3 g.

The amount of oligosaccharides to be included in the supplement will be selected according to the manner in which the supplement is to be administered. For example, if the supplement is to be administered twice a day, each supplement may contain 0.05 to 1.5 g of N-acetyl-lactosamine, 0.05 to 1 g of sialylated oligosaccharide and 0.05 to 1.5 g of fucosylated oligosaccharide.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

An example of the composition of an infant formula according to the present invention is given below. This composition is given by way of illustration only. Another example is based on commercial NAN and/or Lactogen Infant formulae (from Nestle, Switzerland) to which the specific oligosaccharides of the invention are added as in the amount stated below.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (70% FOS, 30% insulin) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| 3'sialyllactose (mg) | 30 | 200 |
| 6'sialyllactose (mg) | 6 | 40 |
| LNnT (mg) | 30 | 200 |
| 2FL (mg) | 300 | 2000 |

EXPERIMENTAL DATA

The following experimental studies (study models 1 and 2) have been performed in relation to the present invention.

The findings as outlined below show that a specific oligosaccharide blend promotes metabolic activity of a lactic acid bacterium (*Bifidobacterium longum* subsp *infantis*) leading to stronger inhibition of a model pathogen. In infants, higher amounts of the oligosaccharide blend in breast milk were associated with less respiratory infections. Together our results suggest that a specific oligosaccharide blend synergistically acts with specific infant commensal bacteria to reduced respiratory infections.

Study Model 1: Stimulation of *Bifidobacterium longum* Subsp *Infantis* and Pathogen Inhibition with Such Conditioned Medium Approach:

*Bifidobacterium longum* subsp *infantis* (ATCC15697) was grown anaerobic in API growth medium supplemented either with 1% (w/v) glucose, or 1% (w/v) 2' fucosyllactose (2FL) or 1% (w/v) lacto-N-neotetrasose (LNnT) or 1% (w/v) 6' sialyllactose (6SL) or 1% (w/v) of a combination of equal amounts of 2FL, LNnT and 6SL. Each overnight culture was diluted to have a starting OD600 of 0.1 in DMEM (Dulbeccos modified Eagle Medium) containing as a carbon source 0.1% glucose. This medium was used without any further carbohydrate supplement or with additional 1% (w/v) glucose, or 1% (w/v) 2' fucosyllactose (2FL) or 1% (w/v) lacto-N-neotetrasose (LNnT) or 1% (w/v) 6' sialyllactose (6SL) or 1% (w/v) of a combination of equal amounts of 2FL, LNnT and 6SL. Conditioning of DMEM media was thus done at 37° C. anaerobic.

After another over night incubation, conditioned media were centrifuged and supernatants filtered through a 0.22 micrometer filter to remove bacteria. Acetate was quantified by HPLC using a Hi-Plex H column and a UV detector.

Thus conditioned DMEM media were adjusted to pH of about 6 to 7 using NaOH and incubated with 10e6 cfu/ml of an overnight grown model pathogen, *Salmonella typhimurium* SL1344. After incubation at 37° C. for 2 hours, pathogens were quantified after plating on LB agar and incubation over night at 37° C.

FIG. 1 illustrates the experimental results showing metabolic stimulation of a bifidobacterium (*B. longum* subsp *infantis*) in DMEM culture medium either without additional carbohydrates or with additional glucose (Glc), or lacto-N-neoteraose (LNnT) or 2' fucosyllactose (2FL) or 6' sialyllactose (6SL) or a blend of LNnT, 6SL and 2FL. (n=6; mean with SEM are shown; significance by ANOVA indicated). Note: Only the blend of LNnT, 6SL and 2FL stimulated significantly the production of acetate.

FIG. 2 illustrates the experimental results showing in vitro growth of a bifidobacterium (*B. longum* subsp *infantis*) in culture medium either without additional carbohydrates or with additional glucose (Glc), or lacto-N-neoteraose (LNnT) or 2 fucosyllactose (2FL) or 2 fucosyllactose (2FL) or 6' sialyllactose (6SL) or a blend of LNnT, 6SL and 2FL. (n=4; mean with SEM are shown; significance by ANOVA (p<0.01) indicated by small letters).

Results:

It has been surprisingly found that an oligosaccharide blend composed of equal parts of a fucoslylated oligosaccharide (e.g. 2'FL), an N-acetylated oligosaccharide (e.g. LNnT) and a sialylated oligosaccharide (e.g. 6SL) significantly increased metabolic activity of a lactic acid bacterium (e.g. *bifidobacterium*), as seen by the formation of acetate (FIG. 1).

Furthermore, the medium conditioned with a *bifidobacterium* and the mentioned oligosaccharide blend also significantly and synergistically inhibited a model pathogen as compared to media that were conditioned with individual oligosaccharides or glucose alone (FIG. 2).

The exact nature of the inhibitory function is not known today, but we propose that the oligosaccharide blend of 2FL, LNNT and 6SL synergizes with bifidobacteria to exert anti-pathogenic effects that are beyond the model pathogen tested here in vitro.

Study Model 2: Retrospective Epidemiologic Analysis of Breast Milk Samples and Occurrence of Respiratory Infections Up to the Age of 2 Years Approach:

From a cohort of about 270 infant mother pairs we analysed early milk samples for amounts of specific oligosaccharides present. To this end defatted milk samples were diluted 10 to 100 times in water and analysed by HPAEC (Dionex) equipped with a CarboPac PA1 column (Dionex) and an electrochemical detector. Oligosaccharide identification and quantification was done with authentic oligosaccharide standards. We plotted number of respiratory infections for infants that were fed milk (i) with low amounts (below 2 g/l) and (ii) with high amounts (more than 2 g/l) of an oligosaccharide blend (composed of 2FL, LNnT, and 6SL).

FIG. 3 illustrates the experimental results showing number of respiratory infections in infants up to 2 years of age that were either fed a milk that contained low amounts (<2 g/l) or high amounts (>2 g/l) of an oligosaccharide blend composed of 2FL, LNnT and 6SL. (statistical significance is indicated).

Results:

It was surprisingly found a significantly reduced number of respiratory infections in the infants that were fed with milk containing higher amounts of the oligosaccharide blend.

The invention claimed is:

1. A method for relieving symptoms of otitis media or bronchiolitis, the method comprising administering a nutritional composition comprising oligosaccharides comprising equal parts of (i) at least one N-acetyl lactosamine comprising lacto-N-neotetraose, (ii) at least one sialylated oligosaccharide comprising 6' sialyllactose, and (iii) at least one fucosylated oligosaccharide comprising 2' fucosyllactose to an infant or young child who suffers from a condition selected from the group consisting of otitis media and bronchiolitis, and at least one of the sialylated oligosaccharide or the fucosylated oligosaccharide is obtained by a process comprising a step selected from the group consisting of isolation from a natural source by filtration, isolation from a natural source by chromatographic technology, chemical synthesis, and biotechnological synthesis.

2. The method according to claim 1, wherein the at least one N-acetyl-lactosamine further comprises lacto-N-tetraose.

3. The method according to claim 1, wherein the at least one sialylated oligosaccharide further comprises 3' sialyllactose.

4. The method according to claim 1, wherein the at least one fucosylated oligosaccharide comprises an additional fucosylated oligosaccharide selected from the group consisting of 3-fucosyllactose, difucosyllactose, lacto-N-fucopentaoses, lacto-N-difucohexaose I, fucosyllacto-N-hexaose, Difucosyllacto-N-hexaose I and Difucosyllacto-N-neohexaose II.

5. The method according to claim 1, wherein the nutritional composition comprises at least one probiotic bacterial strain.

6. The method according to claim 1, wherein the nutritional composition comprises at least one prebiotic.

7. The method according to claim 1, wherein the synthetic nutritional composition comprises at least one phage or a mixture of phages.

8. The method according to claim 1, wherein the nutritional composition is a starter infant formula, an infant formula, a follow-on formula, a baby food formula, an infant cereals formula or a growing-up milk.

9. The method according to claim 1, wherein the infant or young child suffers from otitis media.

10. The method according to claim 1, comprising the step of administering the nutritional composition before and/or during a weaning period.

11. The method according to claim 1, wherein the infant or young child is an infant, and the nutritional composition is administered to ease the breathing process, decrease pain, ease sleep, and/or relieve symptoms in the infant.

12. A method for the treatment of otitis media or bronchiolitis, the method comprising:
administering to an infant or young child who suffers from a condition selected from the group consisting of otitis media and bronchiolitis a nutritional composition comprising equal parts of (i) at least one N-acetyl lactosamine comprising lacto-N-neotetraose, (ii) at least one sialylated oligosaccharide comprising 6' sialyllactose, and (iii) at least one fucosylated oligosaccharide comprising 2' fucosyllactose, and at least one of the sialylated oligosaccharide or the fucosylated oligosaccharide is obtained by a process comprising a step selected from the group consisting of isolation from a natural source by filtration, isolation from a natural source by chromatographic technology, chemical synthesis, and biotechnological synthesis.

13. The method according to claim 1, wherein the nutritional composition is a supplement.

14. The method of claim 1, wherein the nutritional composition comprises hydrolyzed and/or partially hydrolyzed proteins.

15. The method according to claim 1, wherein the nutritional composition is a starter infant formula.

16. The method according to claim 1, wherein the oligosaccharides consist of the lacto-N-neoteraose, the 2' fucosyllactose, and the 6' sialyllactose.

17. The method according to claim 1, wherein the lacto-N-neotetraose is synthesized chemically.

18. The method according to claim 1, wherein isolation from the natural source comprises isolation from an animal milk.

19. The method according to claim 1, wherein a daily dose of the at least one N-acetyl lactosamine is from 0.1 to 3 g.

20. The method according to claim 1, wherein a daily dose of the at least one sialylated oligosaccharide is from 0.1 to 2 g.

21. The method according to claim 1, wherein a daily dose of the at least one fucosylated oligosaccharide is from 0.1 to 3 g.

22. The method according to claim 1, wherein the natural source is animal milk.

* * * * *